United States Patent [19]

Carsalade

[11] Patent Number: 4,617,920
[45] Date of Patent: Oct. 21, 1986

[54] DEVICE FOR FACILITATING THE PRACTICE OF DOWNHILL SKIING

[76] Inventor: Charles Carsalade, 118 rue Crozet Boussingault, 42100 Saint.Etienne, France

[21] Appl. No.: 697,791

[22] Filed: Feb. 4, 1985

[30] Foreign Application Priority Data

Feb. 10, 1984 [FR] France .................. 84 02542

[51] Int. Cl.⁴ .................. A61F 3/00; A41D 13/00
[52] U.S. Cl. .................. 128/80 C; 128/80 F; 2/22; 623/43
[58] Field of Search .......... 128/80 R, 80 C, 80 F; 2/22; 36/117; 623/43, 39

[56] References Cited

U.S. PATENT DOCUMENTS

| | | | |
|---|---|---|---|
| 766,686 | 8/1904 | Gault | 623/43 |
| 1,044,542 | 11/1912 | Lazzara | 128/80 F |
| 1,072,369 | 9/1913 | Spahn | 128/80 F |
| 1,372,365 | 3/1921 | Nevin | 623/43 |
| 2,144,641 | 1/1939 | Snyder | 2/22 X |
| 2,467,907 | 4/1949 | Peckham | 128/80 C |
| 2,557,604 | 6/1951 | Invidiato | 128/80 F |
| 2,632,440 | 3/1953 | Hauser et al. | 128/80 F |
| 3,928,872 | 12/1975 | Johnson | 2/22 |
| 4,136,404 | 1/1979 | Lange | 36/117 X |
| 4,183,099 | 1/1980 | Lacey | 128/80 C X |
| 4,372,298 | 2/1983 | Lerman | 128/80 C |
| 4,450,832 | 5/1984 | Waddell | 128/80 C X |
| 4,487,200 | 12/1984 | Feanny et al. | 128/80 C |

*Primary Examiner*—Clifford D. Crowder
*Attorney, Agent, or Firm*—Steele, Gould & Fried

[57] ABSTRACT

The device for facilitating practice of downhill skiing includes for each lower limb a knee bandage having two suitably curved and profiled plates (13) and (14), one of which (13) wraps up the thigh while the other (14) wraps down the leg, being adapted to cooperate with a part of the user's shoe; the upper plate (13) is continued downward by two opposite and parallel arms (13a) profiled and articulated each on a shaft (4), on either side of the knee, the lower plate (14) being continued upward by two opposite and parallel arms (14b) profiled and articulated around the shaft (4) in combination with upper plate (13), the lower plate being controlled by elastic components to be tensioned, when flexing the knee in combination with appropriate means (7)–(13b), designed to suppress this control beyond a certain flexion angle, said means being fastened to a manual releasing component (11) to fully suppress the elastic control.

8 Claims, 9 Drawing Figures

DEVICE FOR FACILITATING THE PRACTICE OF DOWNHILL SKIING

BACKGROUND OF THE INVENTION

This invention relates to a device for facilitating the practice of downhill skiing especially.

The subject matter of this invention concerns the technical area of sports, more especially equipment for skiing, and to the technical and medical area of devices intended for lower limbs.

It is well known that downhill skiing presents traumatic risks for the lower limbs especially and generates high muscular stresses in the thighs resulting from the most frequently flexed position of the skier's knees. This fact has led to the construction of a device designed to reduce traumatic risks of this sporting activity while increasing safety and providing structural support and assistance to the musculature.

As far as safety is concerned, the device is designed to prevent accidents by increasing the mechanical strength of the lower limb and also allows the practice of skiing for individuals whose limbs may be fragile due to a previous accident, to their age, to the lack of physical training, . . . .

As technical assistance, the device prevents axial rotation of the leg on the knee and provides a better control of ski parallelism, thus avoiding lateral shimmy, which is the cause of many falls.

On the other hand, it is known that lower limb flexion constitutes a basic principle of modern skiing technique. It results in the weight of body being constantly supported by the thigh muscles, which bear high muscular strain in order to face two stresses: on the one hand static stresses, for balancing the body weight, and on the other hand, dynamic stresses for absorbing all the jolts due to the uneven surface of the ground.

The device allows to transfer some of these forces onto an elastic suspension system, thus reducing the fatigue, and therefore the accidents due to this fatigue.

This elastic suspension, because of reasons connected to the skiing technique, is designed so as to be efficient from 10° to 90° knee flexion.

For that purpose, the device comprises, for each lower limb, a knee bandage including two suitably curved and profiled plates made from flexible material, one of which wraps down the leg while the other wraps up the thigh. Both plates are maintained and connected together by two fittings, one inside, the other outside, articulated at the level of the knee. Or, in another embodiment, these two plates are maintained and connected together by being directly articulated at the level of the knee.

The curved lower plate or one part of the relevant fitting is fastened to elastic components adapted to be tensioned when flexing the knee. For that purpose, on either side of the knee, a disk is formed at the bottom of the upper fitting or on an arm projecting downward. A curved upper plate is profiled like a cam, and cooperates with a lever, pivoting around a disk eccentrically mounted on a shaft integral with a part of the fitting or of the lower plate, thus applying tension to the elastic components. An eccentric disk operated by a handle spaces the lever from the cam, thus cancelling the action of the elastic components.

BRIEF DESCRIPTION OF THE DRAWINGS

To determine the object of this invention, without limiting it, in the appended drawings.

DETAILED DESCRIPTION OF THE PREFERRED EMBODIMENTS

The device according to this invention includes for each lower limb a knee bandage consisting mainly of two suitably curved and profiled plates (13) and (14) made from flexible material. Plate (13) wraps partially up the thigh from the knee, while plate (14) wraps partially down the leg from the knee.

Figure 1:
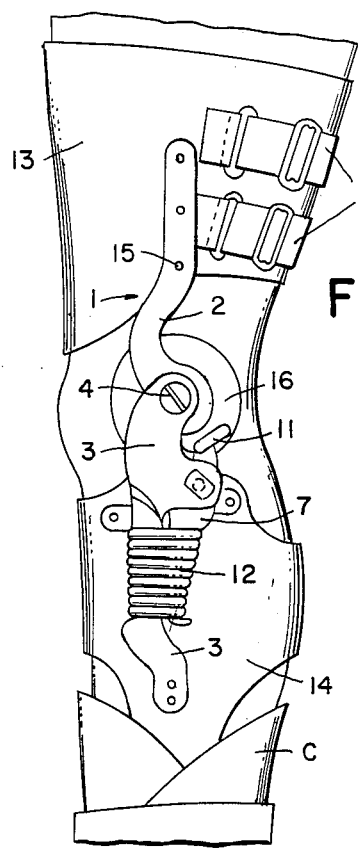
FIGS. 1 and 2 are external section views of the device fitted to a skier's leg and according to a first embodiment of said device.
Figure 2:
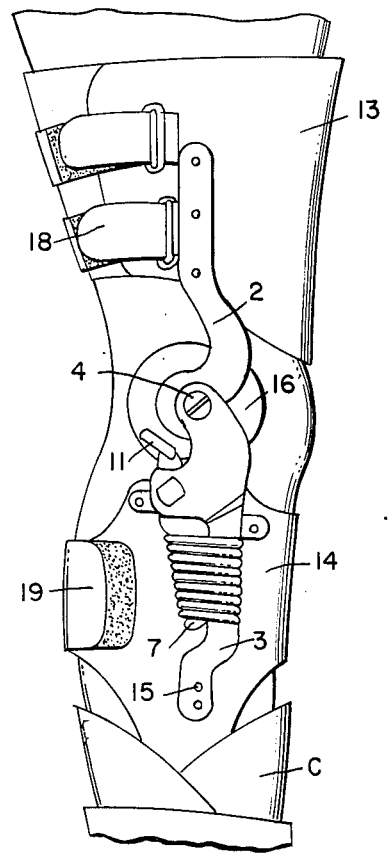
Figure 3:
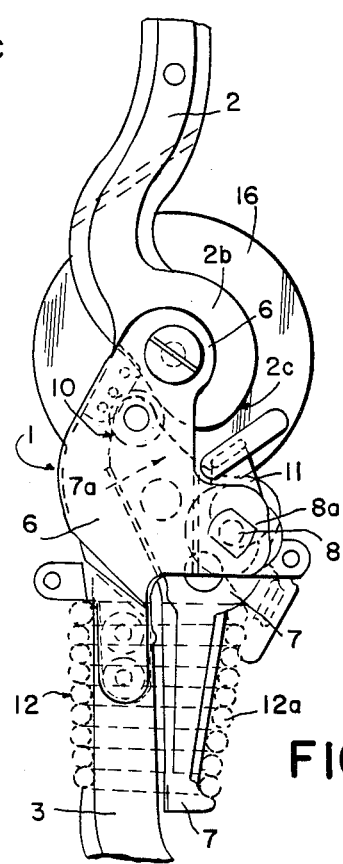
FIG. 3 is, at a greater scale, a partial section view showing the detail of the components of the device mechanism.
Figure 4:
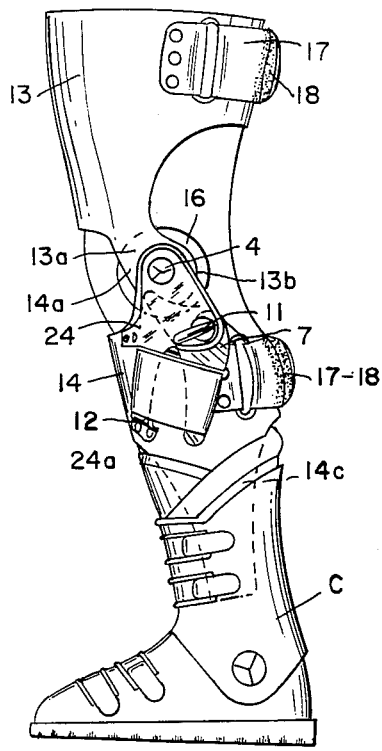
FIG. 4 is a side view of the device fitted to a skier's leg, according to a preferred embodiment of said device.

In the example of the illustrated embodiment, FIGS. 1, 2 and 3, both plates (13) and (14) are maintained and connected together by two fittings (1), one inside, the other outside, articulated at the level of the knee.

For that purpose, each fitting (1) consists of two profiled arms (2) and (3) articulated on a common shaft (4). These two arms (2) and (3) are fastened to a resilient system acting when flexing the limb, in such a way that, under the action of the weight of the body, the angle between the upper (2) and lower (3) arms being reduced, the resilient system is tensioned to partially bear the wearer's body weight as stated in the following description.

The upper arm (2) has at its lower end (2b) a specially shaped profile used as cam (2c). This part of the upper arm is freely articulated on shaft (4) by being maintained between two parallel flanges (6) connecting directly or in an inserted manner with the upper part of arm (3) of the lower plate. Shaft (4) is fixed on flanges (6).

Between flanges (6) below arm (2) is articulated a lever (7) arranged to transfer the suspension stresses by pivoting around shaft (8) on which is angularly indexed an eccentric disk (8a). Lever (7) is designed to accomodate at its end a roller (10) bearing on cam profile (2c) of upper arm (2). The eccentric device (8a) is fastened to a control handle (11) operable to depress manually lever (7) in order to suppress the action of roller (10) opposite the cam profile (2c).

The lower arm (3) is controlled by a resilient system (12) consisting in the example of FIGS. 1, 2 and 3 in a series of rings (12a) made from elastomer, simultaneously enclosing said arm (3) and lower part of articulated lever (7).

The fittings (1) are fixed outside the profiled plates (13) and (14) by means of rivets (15) for instance.

In a preferred embodiment shown in FIGS. 4 to 14, the fittings of the devices are omitted, their maintaining and connecting action being accomplished by curved and profiled plates (13) and (14). The plates are made from resistant enough plastic material, each plate (13)

and (14) being extended by two profiled arms (13a) and (14a), to be articulated on the main shaft (4) on either sides of the knee.

The upper arms (13a) are terminated by a disk (13b) the lower rim of which has an outline of suitable shape used as a cam and adapted to co-operate with a part of lever (7). On either side of the lower leg, the profiled and curved plate (14) is extended downward by two profiled lugs (14c) to be inserted between the skier's leg and a ski shoe or boot, to help to maintain the device.

Figure 5:
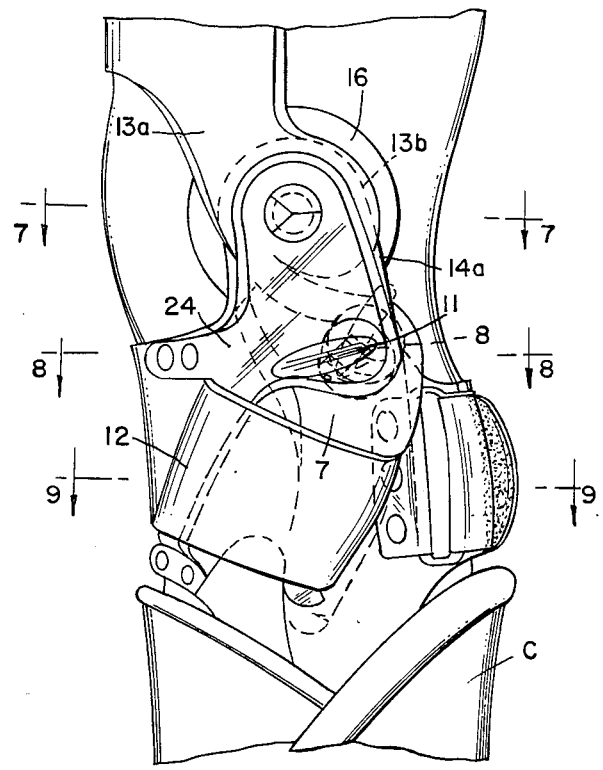
FIG. 5 is an enlarged view of the device shown in FIG. 4, showing the components of the mechanism.
Figure 6:
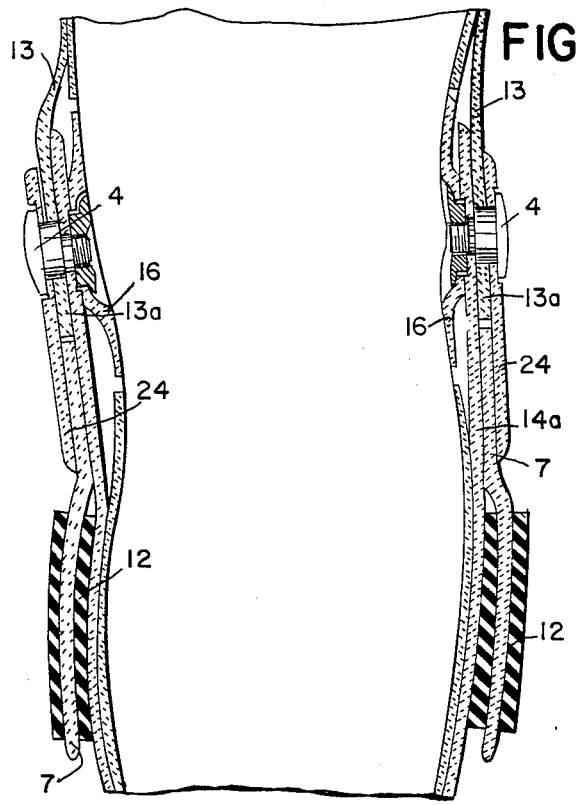
FIG. 6 is a transverse vertical sectional view taken along main lines of the device, shown in FIG. 5.
Figure 7:
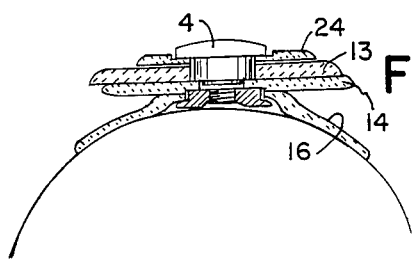
FIGS. 7, 8 and 9 are respectively horizontal sectional views taken along 7—7, 8—8, and 9—9 lines of FIG. 5.
Figure 8:
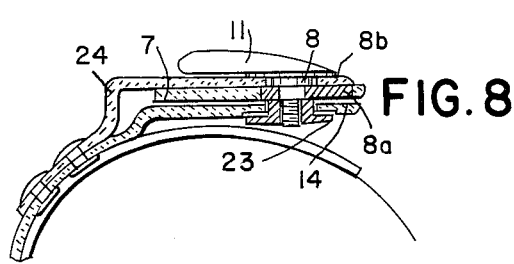
Figure 9:
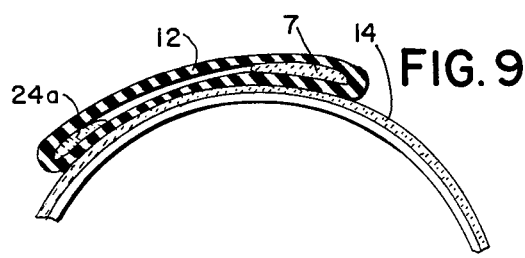

Referring to FIGS. 5 and 8, the eccentric disk (8a) on which is pivotally mounted the lever (7), is angularly indexed on a flat bearing surface (8b) of shaft (8), integral with handle (11). This shaft (8) is rotatably mounted in the thickness of curved plate (14), the whole assembly being maintained by a nut (23). Superposed to lever (7), shaft (8) receives a profiled and bent assembly part (24), fixed to a part of curved plate (14) and pivotable on upper curved plate (13) through shaft (4). This part (24) has at its anterior part and directed downwardly, an arm (24a), fixed on plate (14) while being designed so as to ensure the positioning and holding of elastic components (12). Assembly part (24) and/or arm (24a) are demountable from plate (14).

An elastic suspension device is comprised by the combination of lever (7), able to pivot around eccentric disk (8a) under the action of the cam defined by the profiled lower rim (13b), and of the elastic components (12) which may be made of elastic straps or rubber sleeve, and which are enclosing the basis of lever (7) and arm (24a).

As stated, the position of the disk (8a) is controlled on the shaft by a square-section, the disk being eccentric, and in which is inserted a part of shaft (8) of complementary square section. By acting on handle (11), integral with shaft (8), lever (7) is consequently raised or lowered.

The upper (13) and lower (14) curved plates are fitted with non-elastic straps (17) fitted with adjustable self-gripping systems (18), for maintaining the device on the lower limb with the help of lugs (14c).

The device is still more suitably maintained and comfortable to use thanks to two concave plates (16) with circular outline, made from flexible plastic material, located on either sides of the knee and able to swivel upon shaft (4).

Now the operation of the device is to be described. Under the flexing action of the knee, the curved plate (13) drives the cam (13b) which tips up lever (7) around disk (8a) thus tensioning the elastic component (12). The purpose is to oppose knee flexion and by pressing on cam (13b) to contribute, by spring effect, to the return to 180° of the plate (13) on plate (14), i.e. to align the thigh to the lower leg. Beyond a knee flexion angle of the order of 90°, as the cam radius (13b) becomes constant whereupon, the return action of the elastic component is suppressed, which is a favourable element.

Under some circumstances, especially when walking, it is useful to be able to release the elastic device. For that purpose, it is just necessary to lift handle (11) which, through shaft (8) lowers the eccentric disk (8a) and consequently lever (7) which then stops pressing on cam (13b).

The various components of the device may be made from any materials. For instance, for a minimum weight, all the parts may be made from plastic material.

The shapes of the various parts or components of the device described and/or illustrated are not at all limiting and do not exclude any other one which would be likely to perform the same functions in order to reach the target aimed at.

For instance, the system may be built in a complete assembly including the skier's shoe and thus providing a ski boot, whether the shoe part may or not be separated from the knee holding part, which is the subject matter of this patent.

I claim:

1. A device for facilitating downhill skiing practice, including a knee bandage comprising:
   an upper curved and profiled plate, the upper plate being attachable around a user's thigh;
   a lower curved and profiled plate attachable around the user's lower leg, the lower plate being partly securable by a part of a shoe of the user;
   two opposite and parallel arms extending downwardly from the upper plate, the arms extending from the upper plate being profiled and articulated on a shaft on either side of the user's knee, and two further opposite and parallel arms extending upwardly from the lower plate, the arms extending from the lower plate being profiled and articulated on the shaft with the arms of the upper plate;
   elastic components biasing the upper and lower plates articulated on the shaft, the elastic components being tensioned to oppose flexing of the upper and lower plates up to a certain flexion angle; and,
   means including a manual releasing component operative to fully suppress biasing of the upper and lower plates and relieve the tensioning.

2. A support device for the knee of a user, comprising:
   two curved and profiled plates for attachment to the user's thigh and lower leg adjacent the user's knee, one of the plates wrapping around the thigh while the other of the plates wraps around the lower leg, a lower one of the plates having a part extending downwardly and partly fixable in a shoe of the user both the two plates being connected together by two fittings mounted on either side of the user's leg, each fitting having two profiled arms articulated on a shaft on either side of the user's knee, relative pivoting of the lower plate and the upper plate around the shaft being controlled by elastic components connected to the fittings so as to be increasingly tensioned with increasing flexing of the user's knee up to a certain flexion angle, and further comprising a manual releasing component connected to the fittings and operative to fully relieve tensioning of the elastic components against said plates, and thereby suppress elastic tensioning thereof tending to decrease flexure of the user's knee.

3. A device according to claim 1, wherein the opposite and parallel arms extending from said one of the plates, at the level of articulation around the shaft, has a profile defining a cam and further comprising a lever pivotally mounted around an eccentric disk angularly mounted on a flat bearing surface of said other of the plates by means of a mounting shaft integral with a manual releasing component having a handle, the manual releasing component being operable to press the lever into and out of a position at which the lever engages the cam, whereby the lever is manually and controllably movable against the cam and away from the cam to suppress biasing of the plates and to engage biasing of the plates, respectively.

4. A device according to claim 3, wherein said lever carried on the mounted shaft has a profiled and curved assembly part fastened to part of said other of the curved plates and is articulated to said one of the curved plates through the shaft, the lever being elastically connected to the profiled and curved assembly part, whereby the lever is urged toward the cam.

5. A device according to claim 4, wherein the elastic components enclose both the arm and a lower part of the lever, urging them together.

6. A device according to claim 2, wherein one of the arms has a cam-shaped profile and the arms are pivotally mounted together, and further comprising an eccentric disk angularly indexed toward and away from the cam-shaped profile by means of a releasing component having a handle affixed to said lever.

7. A device according to claim 6, wherein the elastic components include a series of elastomeric rings enclosing and urging together the arm and a lower part of the lever connected for indexing.

8. A device according to claim 1 or claim 2, wherein the upper and lower plates are fitted with adjustable straps attachable together by self-gripping components, the adjustable straps being operable to hold the device on a lower limb of the user, a lower part of the lower plate having two downwardly-extending lugs adapted to be inserted in a shoe.

* * * * *